(12) United States Patent
Howard et al.

(10) Patent No.: US 8,901,326 B2
(45) Date of Patent: Dec. 2, 2014

(54) PREPARATION OF AMINOMETHYL FURANS AND ALKOXYMETHYL FURAN DERIVATIVES FROM CARBOHYDRATES

(71) Applicant: Archer Daniels Midland Company, Decatur, IL (US)

(72) Inventors: Stephen Howard, Sherman, IL (US); Alexandra Sanborn, Lincoln, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/085,080

(22) Filed: Nov. 20, 2013

(65) Prior Publication Data

US 2014/0148605 A1     May 29, 2014

Related U.S. Application Data

(62) Division of application No. 13/994,170, filed as application No. PCT/US2011/064513 on Dec. 13, 2011, now Pat. No. 8,669,383.

(60) Provisional application No. 61/423,684, filed on Dec. 16, 2010.

(51) Int. Cl.

| | |
|---|---|
| *C07D 307/04* | (2006.01) |
| *C07D 307/34* | (2006.01) |
| *C07D 307/42* | (2006.01) |
| *C07D 307/14* | (2006.01) |
| *C07D 307/12* | (2006.01) |
| *C07D 307/44* | (2006.01) |
| *C07D 307/52* | (2006.01) |

(52) U.S. Cl.
CPC ............ *C07D 307/12* (2013.01); *C07D 307/42* (2013.01); *C07D 307/14* (2013.01); *C07D 307/44* (2013.01); *C07D 307/52* (2013.01)
USPC .......................................... 549/502; 549/429

(58) Field of Classification Search
CPC ............................ C07D 307/04; C07D 307/34
USPC .................................................. 549/429, 502
See application file for complete search history.

(56) References Cited

U.S. PATENT DOCUMENTS 8,669,383 B2 *    3/2014    Howard et al. ............... 549/491

* cited by examiner

*Primary Examiner* — Golam M M Shameem
(74) *Attorney, Agent, or Firm* — Alexandra Sanborn; Mark W. Roberts

(57) ABSTRACT

Described herein are single step methods of making various classes of alkylamine derivatives of furan and tetrahydrofuran by simultaneous contact of a sugar with $H_2$, an acid catalyst and hydrogenation catalyst in the presence of an alkylamide solvent. The hydrogenation catalyst is a heterogeneous catalyst comprising a metal selected from the group consisting of Pt, Pd, and nickel. The acid catalysts may be homogeneous mineral acid or a heterogeneous acid catalyst on substrate. In a preferred practice the two catalysts are provided on a common heterogeneous bifunctional support. Using similar combinations of acid and hydrogenation catalysts, there is also described single step methods for making furandimethanol by simultaneously contacting a hexose with the two separate catalysts in the presence of $H_2$ in an aprotic solvent, such as dimethylformamide. With the same catalyst system and similar reaction conditions, 2, 5 furan dialkylethers can also be made in a single step when the solvent includes an ROH alcohol.

12 Claims, 1 Drawing Sheet

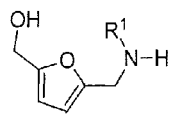

5-[(mono-alkylamino)methyl]furfuryl alcohol

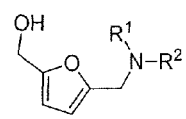

5-[(di-alkylamino)methyl] furfuryl alcohol

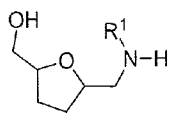

5-[(mono-alkylamino)methyl] 2-tetrahydrofurfuryl alcohol

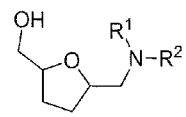

5-[(di-alkylamino)methyl] 2-tetrahydrofurfuryl alcohol

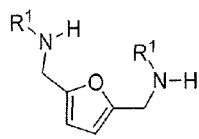

2,5-bis(mono-alkylaminomethyl)furan

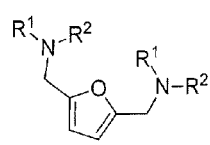

2,5-bis(dialkylaminomethyl)furan

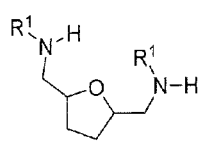

2,5-bis(mono-alkylaminomethyl)tetrahydrofuran

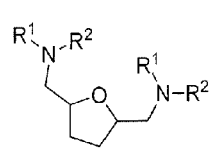

2,5-bis(dialkylaminomethyl)tetrahydrofuran

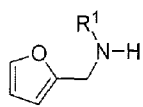

5-[(mono-alkylamino)methyl]furan

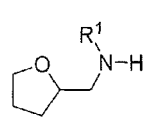

5-[(di-alkylamino)methyl] furan

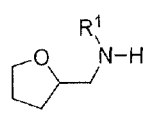

5-[(mono-alkylamino)methyl] 2-tetrahydrofuran

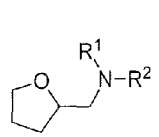

5-[(di-alkylamino)methyl] 2-tetrahydrofuran

PREPARATION OF AMINOMETHYL FURANS AND ALKOXYMETHYL FURAN DERIVATIVES FROM CARBOHYDRATES

CROSS REFERENCE TO RELATED APPLICATIONS

This application is divisional of U.S. application Ser. No. 13/994,170 filed Jun. 14, 2013, which was a national phase entry of PCT application No. PCT/US2011/064513 filed Dec. 13, 2011, which claims priority to U.S. provisional application No. 61/423,684 filed Dec. 16, 2010.

BACKGROUND OF THE INVENTION

The compound 5-(hydroxymethyl)furfural (HMF) is an important intermediate substance readily made from renewable resources, specifically carbohydrates.

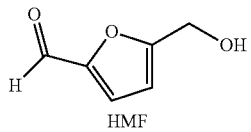

HMF

HMF is a suitable molecule for the formation of various furan ring derivatives that are known intermediates for certain chemical syntheses, and as potential substitutes for benzene based derivatives ordinarily derived from petroleum resources. Due to its various functionalities, it has been proposed that HMF could be utilized to produce a wide range of products such as polymers, solvents, surfactants, pharmaceuticals, and plant protection agents. As substitutes, one may compare derivatives of HMF to chemicals with the corresponding benzene-based rings or to other compounds containing a furan or tetrahydrofuran. HMF and 2,5-disubstituted furans and tetrahydrofuran derivatives, therefore, have great potential in the field of intermediate chemicals from renewable agricultural resources. In order to compete with petroleum based derivatives, however, preparation of HMF derivatives from common agricultural source materials, such as sugars, must be economical.

One of the concerns with HMF, is that it has limited uses as a chemical per se, other than as a source for making derivatives. Furthermore, HMF itself is rather unstable and tends to polymerize and or oxidize with prolonged storage. Due to the instability and limited applications of HMF itself, studies have broadened to include the synthesis and purification of a variety of HMF derivatives. Two derivatives of particular interest include the reduced HMF forms furan-2,5-dimethanol (FDM) and 2,5-bis-(hydroxymethyl)tetrahydrofuran (THF-diol).

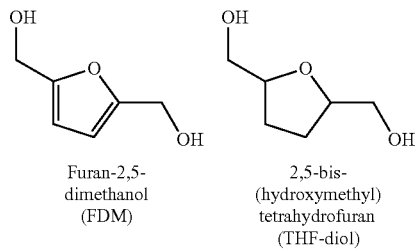 [SMILES: OCc1ccc(CO)o1 ; OCC1CCC(CO)O1]

Furan-2,5-dimethanol (FDM)

2,5-bis-(hydroxymethyl)tetrahydrofuran (THF-diol)

These derivatives have been successfully synthesized in two steps involving the dehydration of fructose to HMF, followed by purification, and subsequent hydrogenation of the purified HMF (see U.S. Pat. No. 7,317,116). Studies have shown HMF, however, that as mentioned above, HMF itself is unstable and is also somewhat difficult to isolate. It would be useful to find a route to synthesis FDM, THF-diol and ether derivatives that did not require the intermediate step of purifying HMF.

Other derivatives of recent interest include HMF secondary and tertiary amines. This class of compounds is useful, for example, as a building block for pharmaceuticals such as ranitidine or Zantac™, which is a well known antiulcer drug. The traditional synthetic route for making ranitidine is according to the following series of reactions:

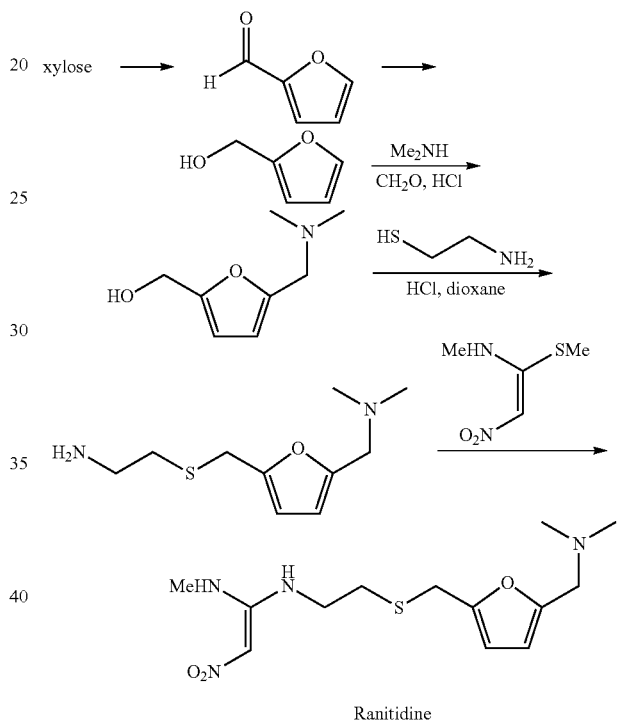

Ranitidine

The fourth compound in this reaction sequence is the HMF derivative 5'-[(dimethylamino)methyl]furfuryl alcohol, which is ordinarily made by reacting 2-hydroxymethyl furan with dimethylamine and formaldehyde as shown in the first line above. The method requires 3 steps to obtain the HMF amine derivative and the use of two hazardous chemicals, dimethylamine and formaldehyde. Dimethylamine is ranked as one of the most the most hazardous compounds (worst 10%) to ecosystems and human health. Formaldehyde also poses health risks with a recommended airborne exposure limit of 0.75 ppm averaged over an 8-hour work shift by the National Institute for Occupational Safety and Health. The National Institute for Occupational Safety and Health's currently sets the short-term exposure limit at 0.1 ppm for 15 minutes. Methods which do not expose humans and the environment to these toxic chemicals are desired for large scale production.

Other furanic secondary and tertiary amines compounds that can be derived from HMF are useful for other purposes, for example, resins, surfactants, and antimicrobial agents. Accordingly, there is a need in the art for efficient and cost effective methods to make furandimethanol, HMF ethers and furanic alkylamino derivatives from inexpensive and less hazardous starting materials.

SUMMARY OF THE INVENTION

The HMF amine derivative, 5-[(dimethylamino)methyl]-furfuryl alcohol, has been successfully synthesized from hexose in single step reaction that uses the simultaneous combination of an acid catalyst and hydrogenation catalyst in the presence of $H_2$ and a polar aprotic solvent. The aprotic solvent exemplified herein is dimethylformamide, however other aprotic solvents could also be used. The two catalysts may be a homogeneous mineral acid catalyst and heterogeneous hydrogenation catalysts, two separate heterogeneous catalysts, one providing the acid functionality and the other the hydrogenation functionality, or most advantageously, using a bifunctional catalyst containing both a metal such as Pt, Pd, and/or Ni for hydrogenation and an acid functionality for acid catalyzed dehydration. The temperature for performing this reaction is between about 90 and 120° C. and the pressure is about 200-600 psi In a similar system, diether derivatives of HMF can also be made using similar reactions where a $C_1$-$C_4$ alcohol is used as the solvent instead of the polar aprotic solvent. These reactions can be performed with the same type of simultaneous catalyst systems described above, but at a temperature of about 100-190° C. at ordinary atmospheric pressure, or in a sealed vessel without the added of $H_2$.

Conversion of the sugar to HMF is accompanied by hydrolysis of the amide solvent, producing an amine functionality which reacts with the aldehyde of HMF generating an imine. The presence of hydrogen and catalyst reduces the imine to an amine yielding the secondary or tertiary amine derivative.

These reactions can be performed with any sugar source including hexoses and pentoses, as well as disaccharides and oligosaccharides of the same.

BRIEF DESCRIPTION OF THE DRAWINGS

FIG. 1 shows subclasses and nomenclature for certain alkyl amide derivatives made according to one aspect of the present disclosure.

DETAILED DESCRIPTION

The present invention is directed most generally, to the discovery that sugars, and most particularly hexoses and pentoses, can be simultaneously dehydrated, reduced, and derivatized to make furan and/or tetrahydrofuran derivatives in a one pot reaction that includes simultaneously contacting the sugar with a hydrogenation catalyst and an acid based catalyst in the presence of hydrogen and a solvent. The selection of the sugar, the solvent and the time, temperature and pressure conditions for the reaction can result in several different classes of derivatized furan or tetrahydrofuran compounds. These can be divided into two aspect: 1) the production of aminomethyl furans or aminomethyl tetrahydrofurans, and 2) the production of furan or tetrahydrofuran dimethanol and ethers thereof.

I Aminomethyl Furan and Aminomethyl Tetrahydrofuran

In a first aspect, there is a method of making either an aminomethylfuran or an aminomethyltetrahydrofuran derivative of the general formulae:

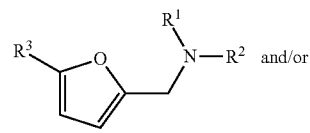

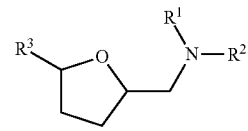

where $R^1$ is a $C_1$-$C_4$ alkyl group, $R^2$ is a $C_1$-$C_4$ alkyl group or H, and $R^3$ is H or hydroxymethyl. Compounds of group I may be generally called alkylaminomethyl furans, where the amine is mono- or dialkylated. Compounds of group II may generally be called alkylaminomethyl tetrahydrofurans. As will be stated in more detail hereafter, the difference between group I and group II compounds is the degree of reduction of the furan, with the group II compound being fully reduced to the tetrahydrofuran.

When the sugar is a hexose or a disaccharide, trisaccharide or oligosaccharide of hexoses, then $R^3$ is a hydroxymethyl group and the compounds of group I would be more specifically denoted alkylamino furans or alternatively 5-alkylamino-2-hydroxymethylfuran (HMF alkylamines) and the compounds of group II would be more specifically denoted alkylamino tetrahydrofuran or alternatively 5-hydroxymethyl tetrahydrofuran-alkylamines ((HMTF alkylamines). When the sugar is a pentose or a disaccharide, trisaccharide or oligosaccharide of pentoses, then $R^3$ is H and the compounds of groups I and II respectively would have the same nomenclature but lacking the 5-hydroxymethyl prefix.

While the forgoing nomenclature is generalized for the group I and group II compounds as a class that can be made by the processes of the present invention, certain specific subclasses of compounds may have other alternative names that would be synonymous with the foregoing general names. An example of some specific classes of the group I and group II compounds with alternative nomenclature that can be made by the methods described herein are shown in FIG. 1.

To obtain molecules of group I and group II, the primary solvent for the reaction system is an amide compound of the general formula:

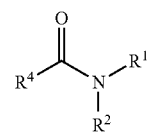

where $R^4$ is H, methyl or ethyl, and $R^1$ and $R^2$ are as previously stated. When $R^4$ is H and $R^1$ and $R^2$ are methyl, for example, the solvent is dimethylformamide (DMF), which is one preferred primary solvent that is readily available in commerce. When $R^4$ is ethyl and $R^1$ and $R^2$ are methyl, the solvent is dimethyl acetamide (DMAC) which is another preferred solvent readily available in commerce. These solvents will react to reductively aminate the sugar to produce the dimethylamino species of the group I and group II molecules. When $R^4$ is H, $R^1$ is methyl, and $R^2$ is H, the solvent is formamide, which is another primary solvent readily available in commerce. When $R^2$ is H the reaction product will be the monomethylamino species of the group I and group II molecules. As indicated above the size of the $R^1$ and $R^2$ alkyl groups may be as long as $C_4$. The size limitation of these alkyl groups for the solvent is only dictated by the solubility of the sugar and the alkylamino furan or tetrahydrofuran products in the primary solvent. In principle however, $R^1$ and $R^2$ can be larger if appropriate co-solvents are used to ensure solubility of the reacting sugar and end products.

As used herein "primary solvent" means the weight of the solvent is at least equal to the weight of the reacting sugar. In various embodiments, the primary solvent represents at least 60%, more preferably at least 80% and more preferably 100% of the added solvent in the system, the last case meaning it is the only solvent added to the system not accounting for solvents that may be present with the sugar or as part of the catalyst. By way of clarity, in reactions where the acid catalyst is a homogeneous mineral acid, the mineral acid is typically an aqueous solution but the water content thereof would not be counted as a solvent per se within the present meaning of the primary solvent being the only added solvent.

Other than the primary solvent, the remaining content of the solvent system may be incidental impurities, or a co-solvent that is miscible with the primary solvent, or a carrier for the catalyst, such as in the case of a homogeneous mineral acid. Any co-solvent should be non reactive under the conditions of pressure and heat in the presence of the $H_2$ and the acid and hydrogenation catalysts used to promote the reaction. Low molecular weight (i.e. non-polymeric) alcohols, aldehydes and organic acid solvents should be avoided as the functional groups on these solvents may cause undesired side reactions. However, certain inert co-solvents such as polyethylene glycols can be used advantageously without perturbing the reaction with the amide solvent. Water may be used in small amounts, including incidental water associated with the sugar or solution of the sugar such as when the sugar is provided as an aqueous syrup solution; however the reaction itself proceeds with an acid catalyzed dehydration of the sugar which adds water to the solvent system. The generated water in turn, facilitates hydrolysis of the amide bond of the solvent, which in the presence of $H_2$ and the hydrogenation catalysts reduces an imine intermediate to the amine product. Too much water however, may slow the reductive amination. Accordingly, the total of amount of water in the reaction system, including that which may be provided by the acid catalyst should, preferably, but not necessarily, be not more than 50% wt/wt.

The temperature and pressure needed to produce the group I and group II products from sugars is about 130° C. to 190° C. and at least 500 psi, respectively. In exemplary embodiments the pressure is 800 to 1000 psi. The only upper limitation on pressure is what the reactor can bear so higher pressures can be used if desired. There is a practical upper limit on temperature, because temperatures greater than about 190° C. will cause char formation. A temperature of about 180° C. is preferred. There is also a chemical reason for the lower limit on the temperature because as discussed below for another aspect of the invention, temperatures below about 130° C. can lead to the preferential formation of another class of reaction products, which can vary dependent on whether the solvent is the amide alone or an amide with an alcohol co-solvent.

It should be noted that because of the high pressure and temperatures used in the reactions and the presence of acid, any monosaccharide, disaccharide or even oligosaccharide sugars can be used as the starting material. The reaction with the acid catalyst in the reaction produces water in the dehydration of the sugar. The water and acid in combination also will hydrolyze glycoside bonds especially at the temperatures and pressures used for the reductive amination. Accordingly, suitable sugars include but are not limited to monosaccharides, disaccharides and oligosaccharides of at least up to 8 residues. Combinations of saccharides or aqueous syrups thereof are also suitable starting materials. The syrups should preferably have a sugar solids content of at least 35% on wt/vol basis. Suitable sugar syrups include for example, corn syrup which contains principally glucose, cane syrup, beet syrup or their molasses, which contain principally sucrose, and high fructose corn syrup, which is a mixture of fructose and glucose in the range of 40-60% fructose to 60-40% glucose obtained by isomerization of a portion of the glucose in ordinary corn syrup.

As stated herein before, the catalysts used simultaneously are a combination of an acid catalyst which promotes dehydration of the sugar, and a hydrogenation catalyst (e.g., Pt, Pd, and/or Ni), which promotes reductive amination of the dehydrated sugar.

In some embodiments the acid catalyst is a homogeneous catalyst, such as a mineral acid. Suitable mineral acid catalysts include sulfuric acid, hydrochloric acid, phosphoric acid and the like. Typically, the mineral acid catalyst is in concentrated form and added to the reaction mixture neat (i.e., at the highest available concentration which is typically 11-18 M), in which case the acid catalyst should be present at about 0.5 to 5% wt/wt basis of the sugar. Of course more dilute acids may also be used provided the acidity in the reaction mixture would be the same as adding 0.5 to 5% wt/wt of the concentrated acid. In exemplary embodiments, the mineral acid is concentrated sulfuric acid present at about 2% wt/wt of the sugar. The acid catalyst may also comprise an organic acid including but not limited to p-toluenesulfonic acid and p-methanesulfonic acid.

In other embodiments the acid catalyst can be a heterogeneous acid catalyst, which is solid material having an acidic group bound to substrate. The solid material can be comprised of materials selected from acid clays, silicas, sulfated zirconia, molecular sieves, zeolites, cation exchange resins, heteropolyacids, carbon, tin oxide, niobia, titania and combinations thereof. Typically the substrate is a polymeric resin material such as polystyrene. The acidic ion exchange resin may also be a sulfonated divinylbenzene/styrene copolymer ion exchange resin. Some of these acid resin based catalysts are ordinarily used for cation exchange chromatography. Perhaps the most common acid group for cation exchange resins and other heterogeneous acid catalyst is a sulfonic group. Suitable examples of heterogeneous acid catalyst containing a sulfonic group are Amberlyst 35, Amberlyst 15, Amberlyst 36, Amberlyst 70, XN 1010, IRC76, and XE586 from Rohm & Haas, RCP21H from Mitsubishi Chemical Corp., Dowex 50WX4 (Dow Chemical Co.), AG50W-X12 (Bio-Rad), and Lewatit S2328, Lweatit K2431, Lewatit S2568, Lewatit K2629 (Bayer Corporation), HPK25 (Mitsubishi), Nafion-50 (DuPont). Other acid groups bound to substrates may also be used as the heterogeneous acid catalyst. Suitable examples of other acidic heterogeneous acid catalyst include CRP-200 phosphonic/polystyrene (Rohm & Haas).

The hydrogenation catalyst is one containing a metal that is Pt, Pd, or NI, however, Co, Cu, Ru, Re, Rh, Ir, Fe and/or combinations of the same, with or without a promoter metal may also be employed. In some embodiments, the metal may be added to the mixture as a heterogeneous particulate powder. In more typical embodiments, the metal is bound to a substrate forming a heterogeneous metal catalyst substrate. Typical substrates include, but are not limited to kieselguhr, diatomaceous earth, silica and polymeric resin materials. One exemplary metal catalyst is represented by G-69B, available from Sud-Chemie, (Louisville, Ky.) which is a powdered catalyst having an average particle size of 10-14 microns containing nominally 62% Nickel on kieselguhr, with a Zr promoter. Other suitable catalysts containing Ni include, but are not limited to, sponge nickel and G-968 also available from Sud-Chemie Corp. G-96B is a nickel on silica/alumina, 66% nickel by weight, particle size 6-8 microns. Another preferred nickel catalyst is G-49B available from Sud-Chemie Corp. Particle size is 7-11 microns and 55% nickel by weight. Another preferred catalyst is palladium on carbon, exemplified by the catalyst Pd/C. Another preferred catalyst is G22/2 also available from Sud-Chemie Corp. G22/2 is a barium promoted copper chromite catalyst, 39% Cu and 24% Cr. In yet another embodiment the catalyst can be a platinum catalyst, exemplified by the catalyst Pt/C. In a preferred embodiment, the acid catalyst and the hydrogenation catalyst are provided on the same substrate, forming a heterogeneous bifunctional catalyst. Exemplary catalyst of this nature include Amberlyst™ CH10 and CH28, each available from Rohm and Haas Company (Midland, Mich.). Amberlyst CH10 is a macroreticular palladium metal hydrogenation resin containing sulfonic acid as the acid component. Amberlyst CH28 is a macroreticular styrene DVB copolymer palladium doped hydrogenation resin also containing sulfonic acid as the acid component. The present invention utilizes these exemplary resins as bifunctional catalysts, i.e., the palladium catalyzes hydrogenation, while the sulfonic acid promotes dehydration in one pot. This use of a bifunctional catalyst system for conversion of sugars to furan or tetrahydrofuran derivatives provides for efficient one pot conversion of sugars into useful chemicals.

The amount of hydrogenation catalyst to use can be readily optimized based on the teachings provided herein. Generally, the hydrogenation catalyst on whatever support used, should be present at about 1% to about 40% wt/wt of the amount of sugar being converted. In exemplary embodiments the Ni catalyst G-69B was used at 5% wt/wt the amount of sugar in the reaction mixture, while the bifunctional catalysts CH28 or CH10 were used at 20-33% of the weight of sugar being converted. Using any of the several embodiments of catalysts indicated above, molecules of group I or II can be made at the principle product of a sugar. The difference in conditions for obtaining the group I and group II compounds is principally time, although higher $H_2$ pressure and hydrogenation catalyst selection will also enhance further reduction. The group I aminomethyl furansaminomethyl furans are less reduced than the group II aminomethyl tetrahydrofuransaminomethyl furansaminomethyl tetrahydrofurans. Accordingly, in a reaction sequence the group I compounds will be formed first. Under an exemplary reaction at 175-180° C., 800-1000 psi, in the presence of DMF as the solvent with fructose as the sugar using a nickel containing hydrogenation catalyst such as G-69B resin and sulfuric acid as the acid catalyst, the dominant product will be the group I aminomethyl furans after 1.5 to 3 hours of reaction time. If the reaction proceeds further, the furan derivative will become further reduced to the group II aminomethyl tetrahydrofuran derivatives. Similarly, a more active hydrogenation catalyst can produce group II compounds in shorter amount of time. It was observed that the reactions that produce the group I aminomethyl furans and group II aminomethyl tetrahydrofurans also may result in the production of smaller amounts of secondary-products, which are bis(amine) derivatives of the group I and group II compounds. Accordingly, another aspect of the present disclosure is use of the aforementioned methods to produce the following class of compounds:

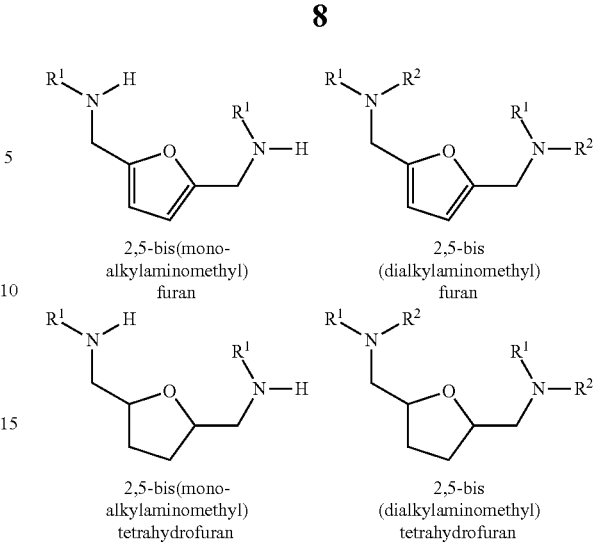

2,5-bis(mono-alkylaminomethyl) furan 2,5-bis(dialkylaminomethyl) furan 2,5-bis(mono-alkylaminomethyl) tetrahydrofuran 2,5-bis(dialkylaminomethyl) tetrahydrofuran These bis(amine) derivatives of the group I and group II compounds are made when the sugar is a hexose, in which case $R^3$ is hydroxymethyl and the alcohol moiety $R^3$ is also subject to reductive amination. Reaction conditions that include use of stronger acids, dryer conditions (have less water) and longer times seem to improve formation of these bis(amine) derivatives.

Taking these together with the compounds shown in FIG. 1, when the sugar is a hexose or a saccharide thereof, the first aspect of the present invention is capable of making one or more classes of compounds from the following list: 5-[(mono-alkylamino)methyl]furfuryl alcohol, 5-[(di-alkylamino)methyl]furfuryl alcohol, 5-[(mono-alkylamino)methyl]2-tetrahydrofurfuryl alcohol, 5-[(di-alkylamino)methyl] 2-tetrahydrofurfuryl alcohol, bis(mono-alkylaminomethyl)furan, bis(dialkylaminomethyl)furan, bis(mono-alkylaminomethyl)tetrahydrofuran, bis(dialkylaminomethyl)furan and bis(dialkylaminomethyl)tetrahydrofuran.

When the sugar is a pentose or a saccharide thereof, the first aspect of the present invention is also capable of making one or more compounds from the following list: 5-[(mono-alkylamino)methyl]furan, 5-[(di-alkylamino)methyl]furan, 5-[(mono-alkylamino)methyl]2-tetrahydrofuran and 5-[(di-alkylamino)methyl]2-tetrahydrofuran.

II Furan and Tetrahydrofuran Dimethanol and Ethers

It also was discovered that with a hexose sugar, when DMF was used as the solvent, with bifunctional catalyst, when the temperature was less than 130° C. and the pressure was 600 psi or less, but otherwise under similar reaction conditions described above for making the alkylamine derivatives, that instead of the alkylamine, furan dimethanol and tetrahydrofuran dimethanol were made having the formulae:

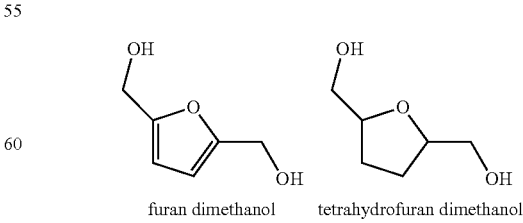

furan dimethanol    tetrahydrofuran dimethanol

These dimethanol compounds are formed when the sugar is a hexose. If the sugar is a pentose the mono methanol-furan and monomethanol tetrahydrofuan derivatives are made instead.

To make furan dimethanol, the hexose is contacted with $H_2$, a bifunctional catalyst containing a metal in the presence of DMF at temperature of between about 90 and 120° C. and a pressure of between about 200 to 600 psi for a time sufficient to produce furan dimethanol. In exemplary embodiments, the temperature was 100° C., the pressure was 500 psi, and the time was three hours. To make the tetrahydrofuran dimethanol, the time should be longer. When the solvent system lacks the amide solvent but instead contains an alcohol R' OH where R is $C_1$-$C_4$ alkyl, the product is a dialkyl ether of the furan or dialkyl ether of tetrahydrofuran according to group III or group IV, respectively.

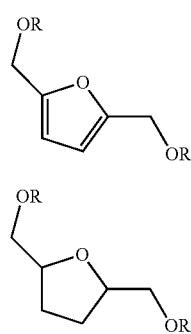

The following examples are provided as illustrations to teach one of ordinary skill in the art some basic methods for practicing the inventions of the present disclosure, with the recognition that altering parameters and conditions, for example by changing temperature, time and reagent amounts and particular amides, alcohols, sugars and specific catalysts and amounts thereof, the full practice of the invention can be extended beyond the limits of the examples provided for illustrative purposes.

EXAMPLE 1

Preparation of HMF Amine from Fructose Using a Combination of Catalysts

This example illustrates the combination of single catalysts on the simultaneous dehydration of fructose to HMF followed by reductive amination. Crystalline fructose (10 g) was placed in a 100 mL reaction vessel with DMF (60 mL) and G-69B catalyst from Sud Chemie (0.50 g) and sulfuric acid (0.20 mL) and pressurized to 800 psi hydrogen. The solution was heated to 180° C. for 1.5 hours. The reaction was allowed to cool to ambient temperature and filtered to remove the catalyst. GC/MS analysis showed formation of 5-[(dimethylamino)methyl]-furfuryl alcohol as the major product and bis(dimethylaminomethyl)furan as a secondary by-product.

EXAMPLE 2

Preparation of HMF Amine from Fructose Using a Combination of Catalysts

This example illustrates the combination of single catalysts on the simultaneous dehydration of fructose to HMF followed by reductive amination. Crystalline fructose (30 g) was placed in a 1000 mL reaction vessel with DMF (300 mL) and G-69B catalyst from Sud Chemie (2.40 g) and sulfuric acid (0.60 mL) and pressurized to 800 psi hydrogen. The solution was heated to 175° C. for 2 hours. The reaction was allowed to cool to ambient temperature and filtered to remove the catalyst. GC/MS showed formation of 5-[(dimethylamino) methyl]-furfuryl alcohol.

EXAMPLE 3

Synthesis of HMF Amines from Fructose Using Bifunctional Catalysts

Crystalline fructose (30 g) was placed in a 1 L reaction vessel with dimethylformamide (300 g) and CH10 resin (10 g). The solution was heated to 140-150° C. for 2 hours. The solution was allowed to cool to room temperature and filtered to remove the resin catalyst. GC/MS and 1H NMR supported the formation of 5-[(dimethylamino)methyl]-furfuryl alcohol.

EXAMPLE 4

Synthesis of HMF Amines from Fructose in an Inert Solvent

Crystalline fructose (10 g) was placed in a 100 mL reaction vessel with PEGE-500 (50 g), (a polyethylene glycol dimethyl ether polymer having an average molecular weight of about 500), dimethylformamide (13 g), sulfuric acid (0.20 mL), and G-69B catalyst (0.50 g). The solution was heated to 180° C. for 3 hours. The solution was allowed to cool to room temperature and filtered to remove the resin catalyst. GC/MS indicated complete conversion of fructose and formation of 5-[(dimethylamino)methyl]-furfuryl alcohol.

EXAMPLE 5

Synthesis of HMF Amines from Fructose Using a Combination of Catalysts

Crystalline fructose (10 g) was placed in a 100 mL reaction vessel with 3.7% $H_2SO_4$ (db), 5.0% G-69B catalyst (db) and pressurized to 1000 psi $H_2$ at 180° C. for 3 hrs. The solution was allowed to cool to room temperature and filtered to remove the catalyst. GC/MS indicated complete conversion of fructose and formation of 5-[(dimethylamino)methyl]-furfuryl alcohol and bis(dimethylaminomethyl)furan.

EXAMPLE 6

Preparation of FDM from Fructose

This example illustrates the effect of bifunctional resin on the dehydration of fructose to HMF followed by reduction to give furan dimethanol (FDM). Crystalline fructose (50.21 g) was placed in a 1 L reaction vessel with DMF (500 mL) and CH10 resin from Rohm and Haas (10.36 g) and pressurized to 500 psi hydrogen. The solution was heated to 100° C. for 3 hours. The reaction was allowed to cool to ambient temperature and filtered to remove the resin. GC/MS confirmed the formation of FDM.

EXAMPLE 7

Synthesis of Reduced HMF Ether Derivative from Fructose

Crystalline fructose (30 g) was placed in a 1 L reaction vessel with ethanol (300 g) and CH28 resin (10 g). The solution was heated to 130° C. for 2 hours at 800 psi $H_2$. The solution was allowed to cool to room temperature, filtered to remove the resin catalyst, and ethanol was removed by rotary evaporation. GC/MS indicated formation of the 2,5-bis-(ethoxymethyl)tetrahydrofuran.

The foregoing examples are by way of illustration only and are not intended to limit the present invention in any way. In particular, although the amide solvent used in the examples was DMF, any amide of the formulas previously stated herein would form different alkyl amide derivatives with similar facility. Likewise, although the exemplary formation of the ether was with use of ethanol as the solvent, any other alcohol as previously mentioned herein could also be used and result in a different alkoxymethylfuran derivative. Moreover, even though the examples illustrate formation of the furan derivatives, the conditions are such that with extended time, the tetrahydrofuran derivatives would also be made. Accordingly, the invention may only be limited in accordance with the claims that follow.

What is claimed is:

1. A method for making a 2,5-dihydroxymethylfuran or a 2,5-dihydroxymethyl tetrahydrofuran derivative compound of a formula selected from the group consisting of:

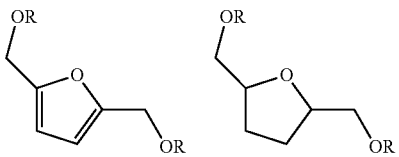

where R is H or a $C_1$-$C_4$ alkyl group;
comprising, contacting the hexose in an organic solvent with a hydrogenation catalyst containing a metal comprising a member selected from the group consisting of Pd, Pt and Ni, and simultaneously with an acid catalyst, at a temperature, a pressure and for a time sufficient to dehydrate the sugar and reduce the dehydrated product to the hydroxymethylfuran or hydroxymethyltetrahydrofuran derivative.

2. The method of claim 1 wherein the organic solvent is a polar aprotic solvent, the reaction mixture further includes $H_2$ the temperature is 90-120° C., the pressure is 200-500 psi, and the hydroxymethylfuran or tetrahydrofuran derivative is furandimethanol or tetrahydrofuran dimethanol.

3. The method of claim 2 wherein the pressure is 400-600 psi, and the time is 2-6 hours.

4. The method of claim 2 wherein the polar aprotic solvent comprises dimethylformamide.

5. The method of claim 1 wherein the organic solvent is a C1-C4 alcohol and the hydroxymethylfuran or tetrahydrofuran derivative is a 2,5-furandiether or a 2,5-tetrahydrofuran diether.

6. The method of claim 5 wherein the temperature is 110-160 C, the pressure is greater than 400 psi, and the time is 1-4 hours.

7. The method of claim 1 wherein the hydrogenation catalyst is a heterogeneous catalyst and the acid catalyst is a homogeneous mineral acid catalyst.

8. The method of claim 1 wherein the hydrogenation catalyst and the acid catalyst are heterogeneous catalysts.

9. The method of claim 1 wherein the hydrogenation catalyst and the acid catalyst serve as a bifunctional catalytic system, both immobilized on a common solid support.

10. The method of claim 1 wherein the hydrogenation catalyst is a heterogeneous catalyst and the metal comprises Pd.

11. The method of claim 1 wherein the hydrogenation catalyst is a heterogeneous catalyst comprising Pd and the acid catalyst is a heterogeneous catalysts comprising sulfonic acid.

12. The method of claim 11 wherein the hydrogenation catalyst and the acid catalyst serve as a bifunctional catalytic system, both immobilized on a common solid.

* * * * *